(12) United States Patent
Geros

(10) Patent No.: US 8,273,559 B2
(45) Date of Patent: Sep. 25, 2012

(54) METHOD FOR THE PRODUCTION OF CONCENTRATED ALCOHOL FROM FERMENTATION BROTHS

(75) Inventor: David George Geros, Ottawa (CA)

(73) Assignee: Iogen Energy Corporation, Ontario (CA)

( * ) Notice: Subject to any disclaimer, the term of this patent is extended or adjusted under 35 U.S.C. 154(b) by 483 days.

(21) Appl. No.: 12/548,811

(22) Filed: Aug. 27, 2009

(65) Prior Publication Data

US 2010/0055753 A1    Mar. 4, 2010

Related U.S. Application Data

(60) Provisional application No. 61/092,769, filed on Aug. 29, 2008.

(51) Int. Cl.
*C12P 7/10* (2006.01)
*B01D 3/28* (2006.01)
*C07C 29/80* (2006.01)

(52) U.S. Cl. .............................. 435/161; 203/34; 203/18

(58) Field of Classification Search .................. 435/161; 203/34, 18
See application file for complete search history.

(56) References Cited

U.S. PATENT DOCUMENTS

| | | | |
|---|---|---|---|
| 2,614,072 A | 10/1952 | Carlson et al. | |
| 2,626,284 A | 1/1953 | Smith | |
| 2,953,502 A | 9/1960 | Binning et al. | |
| 3,689,371 A | 9/1972 | Kerber et al. | |
| 3,960,672 A | 6/1976 | Ester et al. | |
| 3,990,952 A | 11/1976 | Katzen et al. | |
| 4,384,924 A | 5/1983 | Thoma | |
| 4,448,644 A | 5/1984 | Foster et al. | |
| 4,659,590 A | 4/1987 | Neidlinger et al. | |
| 5,554,286 A | 9/1996 | Okamoto et al. | |
| 6,638,398 B1 | 10/2003 | Ramm-Schmidt et al. | |
| 2006/0243584 A1 | 11/2006 | Reutemann et al. | |
| 2008/0057555 A1* | 3/2008 | Nguyen ........................ 435/165 |

FOREIGN PATENT DOCUMENTS

WO    98/58071    12/1998
WO    WO 2007130337 A1 *  11/2007

OTHER PUBLICATIONS

Lynd, et al., "Fuel Ethanol from Cellulosic Biomass", Science, vol. 251 (1991) 1318-1323.
Tolan, "Iogen's process for producing ethanol from cellulosic biomass", Clean Techn Envrion Policy, vol. 3 (2002) 339-345.

* cited by examiner

*Primary Examiner* — Rosanne Kosson
(74) *Attorney, Agent, or Firm* — Fitzpatrick, Cella, Harper & Scinto

(57) ABSTRACT

A method for obtaining a concentrated alcohol solution from a lignocellulosic feedstock. The lignocellulosic feedstock is hydrolyzed to prepare a sugar solution. The sugar solution is fermented to produce a fermentation broth comprising alcohol and at least about 1 g ammonium ions/kg fermentation broth. The alcohol in the fermentation broth is then concentrated by distillation to produce an alcohol-enriched vapour. Either before distillation, during distillation or during the azeotrope breaking process, the concentration of ammonia in the alcohol-enriched vapour can be reduced by acid addition to at most about 300 ppm. The alcohol in the alcohol-rich vapour is then further concentrated by an azeotrope breaking process to provide the concentrated alcohol solution.

37 Claims, 1 Drawing Sheet

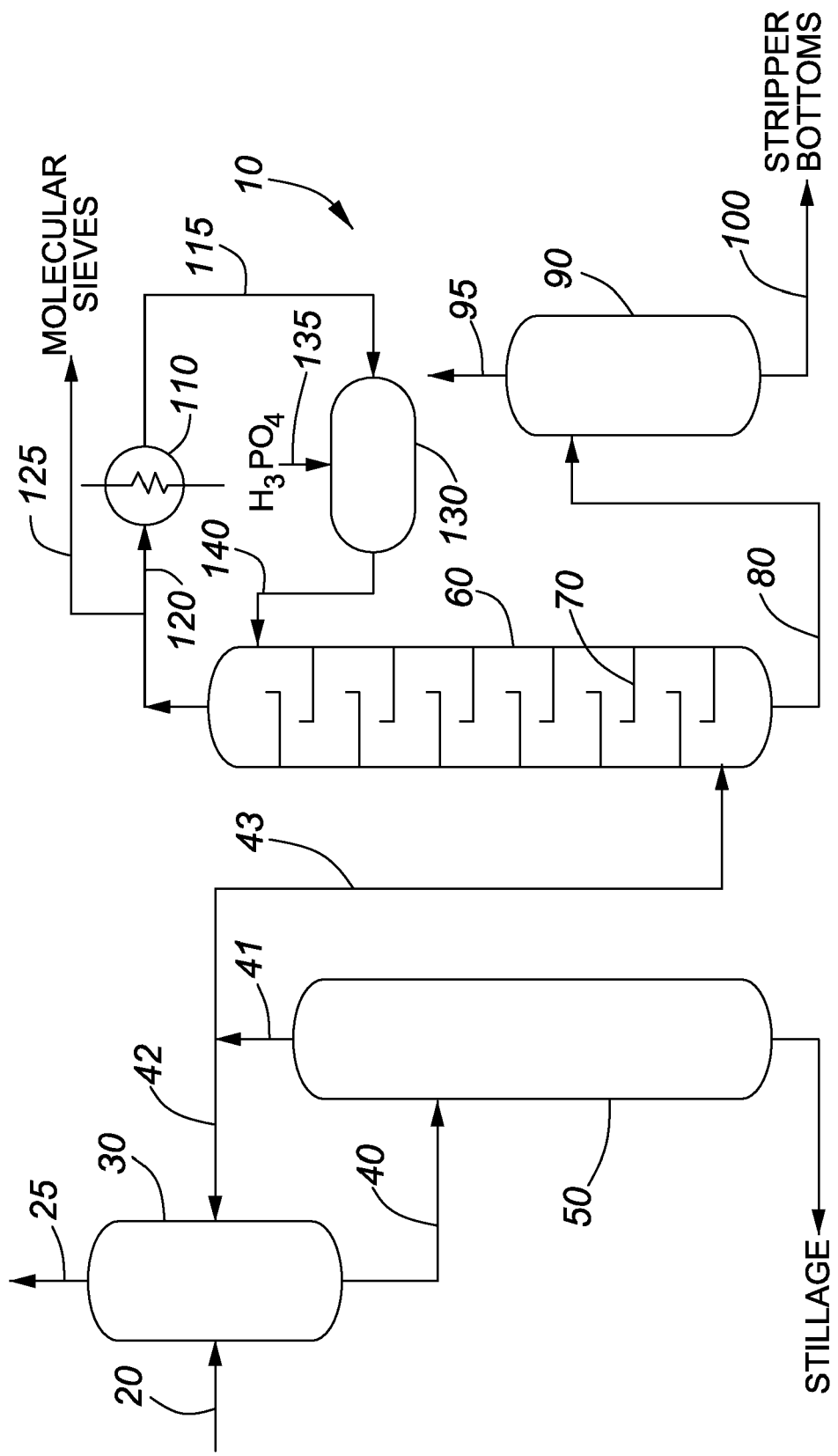

METHOD FOR THE PRODUCTION OF CONCENTRATED ALCOHOL FROM FERMENTATION BROTHS

FIELD OF THE INVENTION

The present invention relates to an improved method for obtaining concentrated alcohol. More specifically, the present invention relates to the production of concentrated alcohol obtained after distillation of a fermentation broth.

RELATED ART

Fuel ethanol is currently produced from feedstocks such as corn starch and sucrose derived from sugar cane and sugar beets. However, the potential for production of ethanol from these sources is limited as most of the farmland which is suitable for the production of these crops is already in use as a food source for humans. Furthermore, the production of ethanol from these feedstocks produces greenhouse gases because fossil fuels are used in the conversion process.

The production of ethanol from lignocellulosic feedstocks, such as agricultural wastes, grasses, and forestry wastes, has received much attention in recent years. The reasons for this are that these feedstocks are widely available and inexpensive and their use for ethanol production provides an alternative to burning or landfilling lignocellulosic waste materials. Moreover, a byproduct of lignocellulosic feedstock conversion, lignin, can be used as a fuel to power the process instead of fossil fuels. Several studies have concluded that, when the entire production and consumption cycle is taken into account, the use of ethanol produced from lignocellulosic feedstocks generates close to zero net greenhouse gases.

The three primary constituents of lignocellulosic feedstocks are cellulose, which makes up about 20% to about 50% of most of the key feedstocks; hemicellulose, which makes up about 15% to about 35% of most feedstocks, and lignin, which makes up about 10% to about 30% of most feedstocks. Cellulose and hemicellulose are comprised primarily of carbohydrates and are the source of sugars that can potentially be fermented to ethanol. Lignin is a phenylpropane lattice that is not converted to ethanol.

Cellulose is a polymer of glucose with beta-1,4 linkages and this structure is common among the feedstocks of interest. Hemicellulose has a more complex structure that varies among the feedstocks. For the feedstocks which are typically of interest, the hemicellulose typically consists of a backbone polymer of xylose with beta-1,4 linkages, with side chains of 1 to 5 arabinose units with alpha-1,3 linkages, or acetyl moieties, or other organic acid moieties such as glucuronyl groups.

The first process step for converting lignocellulosic feedstock to ethanol or other alcohol products involves breaking down the fibrous material. This generally involves the use of steam or heated water along with acid or alkali to break down the fibrous material. The chemical treatment is carried out either as a direct conversion process termed acid or alkali hydrolysis, or as a pretreatment prior to enzymatic hydrolysis with cellulase enzymes.

In the acid or alkali hydrolysis process, the feedstock is subjected to steam and acid or alkali under conditions sufficient to hydrolyze the cellulose and hemicellulose to their monomeric constituents, which is glucose from cellulose and xylose, galactose, mannose, arabinose, acetic acid, galacturonic acid, and glucuronic acid from hemicellulose. If sulfuric acid is employed, it can be concentrated (about 25% to 80% w/w) or dilute (about 3% to 8% w/w). The resulting aqueous slurry contains unhydrolyzed fiber that is primarily lignin, and an aqueous solution of glucose, xylose, organic acids, including primarily acetic acid, but also glucuronic acid, formic acid, lactic acid and galacturonic acid, and the mineral acid.

In the case of acid pretreatment, much of the hemicellulose is hydrolyzed, but there is little conversion of the cellulose to glucose. The cellulose is hydrolyzed to glucose in a subsequent step that uses cellulase enzymes, and the acid hydrolysis step in this case is known as pretreatment. Alkali pretreatment methods may or may not hydrolyze hemicellulose. In either case, the base reacts with acidic groups present on the hemicellulose to open up the surface of the substrate. In addition, it has been reported that pretreatment with alkali may alter the crystal structure of the cellulose so that it is more amenable to hydrolysis. The cellulose is then typically hydrolyzed to glucose in a subsequent step that uses cellulase enzymes, although it is possible to hydrolyze the cellulose, in addition to the hemicellulose, using acid hydrolysis after alkali pretreatment. The hydrolysis of the cellulose, whether by acid, alkali or by pretreatment followed by enzymatic hydrolysis, is followed by the fermentation of the sugar to alcohol.

If an alcohol, such as ethanol, is the desired product from the fermentation, it is often recovered from the fermentation broth, or "beer", by distillation. This is typically effected by removing carbon dioxide from the beer and then pumping the beer through one or more distillation columns to separate the alcohol from other components present. In the production of fuel ethanol, it is necessary to remove a substantial portion of the water from the product to prevent phase separation when blended with gasoline. For ethanol solutions containing above about 95.6 wt % ethanol, standard distillation cannot remove the residual water since this is the azeotropic concentration at which standard distillation becomes ineffective. However, the residual water may be removed by "breaking" the azeotrope using azeotropic breaking processes. It is common in the production of fuel ethanol to concentrate the ethanol in the beer by distillation to produce an ethanol-enriched vapour and to feed this vapour to the azeotropic breaking process. One known azeotropic breaking process utilizes a desiccant which adsorbs water, while allowing ethanol in the feed stream to pass. Such desiccants, referred to as molecular sieves, commonly utilize synthetic zeolites that have a crystalline lattice structure that contains openings of a precise size, usually measured in angstroms. Other methods to break the azeotrope include pervaporation and the addition of an additional component to the mixture, such as benzene or cyclohexane. See, for instance, U.S. Pat. Nos. 2,953,502, 4,659,590 and 5,554,286.

Depending on the chemicals used during processing of the feedstock, ammonium salts may be produced. For example, prior to the addition of cellulase enzymes, it is typically necessary to neutralize acid pretreated feedstock with alkali. It is known to use sodium hydroxide, potassium carbonate, potassium bicarbonate, sodium carbonate, sodium bicarbonate, ammonia and ammonium hydroxide for this purpose. When ammonia or ammonium hydroxide is employed to adjust the pH, this neutralization step generates ammonium salts. Furthermore, when ammonia or ammonium hydroxide is used in alkali pretreatment, neutralization with acid prior to cellulase hydrolysis produces ammonium salts. Full alkali hydrolysis of the cellulose and hemicellulose components of the lignocellulosic feedstock with ammonia or ammonium hydroxide and subsequent pH adjustment of the hydrolysate with acid also leads to production of ammonium salts.

The inventor has discovered that in processing lignocellulosic feedstock to produce an alcohol, wherein ammonium salts or a combination of ammonium salts and ammonia are present in the processing system, the concentration of ammonium ions in the fermentation broth may be sufficiently high to give rise to the presence of ammonia in the alcohol-enriched vapour that is fed to the azeotropic breaking process and a consequent reduction in the performance of the azeotropic breaking process. The concentration of ammonium ions in the beer that leads to a reduction in performance of the azeotropic breaking process depends on process operating conditions and may be equal to or greater than about 1 g/kg, about 1.5 g/kg, about 2 g/kg or about 3 g/kg.

Moreover, in the case of fuel ethanol, current buyers require that its $pH_e$ (pH of the resulting concentrated ethanol) is within a defined pH range. Traditionally, in ethanol produced from starch or sucrose, the $pH_e$ is low and can be adjusted by caustic addition to the distillation column or by additives to the distillate. The inventor has found, however, that if the concentration of ammonium ions in the beer is sufficiently high, as noted above, the $pH_e$ of the concentrated ethanol may be too high due to the presence of ammonia.

It is conventional in the distillation industry to remove impurities which affect product purity by the addition of alkali to the feed to distillation processes or during distillation. Such alkali addition steps cause neutralization of the impurities thereby forming salts, which can then be removed as a bottoms product due to their reduced volatility and solubility in water. Examples of processes that employ alkali addition are disclosed in U.S. Pat. Nos. 3,990,952, 2,626,284, 3,689,371, 2,614,072 and 3,960,672. It is also known to add alkali during distillation to reduce the corrosion of distillation columns by harshly acidic streams. (See, for example, U.S. Publication No. 2006/0243584).

The use of acid in evaporation processes has been disclosed to remove ammonia as set forth in U.S. Pat. No. 6,638,398. Due to the addition of the acid, the ammonia is neutralized into a less volatile, water-soluble salt form, thereby preventing the formation of an inert gas layer of ammonia on a condenser. The evaporated vapour may arise from aqueous solutions rich in ammonia, such as effluents from the chemical industry, the slaughtering industry and agriculture, leachate water from landfills and sludge digestion press waters from urban waste water purification plants. Therefore, in such a process the object is not to isolate a high purity alcohol product, but rather merely to evaporate and concentrate effluent streams.

Likewise, U.S. Pat. No. 4,384,924 discloses a process for concentrating volatile acids or bases from waste water resulting from the production of nitroguanidine, a chemical used in explosives and for making pesticides. A process is described therein in which urea and ammonium nitrate are reacted to form guanidine nitrate, which in turn is used produce the nitroguanidine. During the reaction, to maintain the reaction melt in a liquid state and to avoid the production of considerable quantities of triazine byproducts, the presence of excess ammonium nitrate in the reaction is necessary. Nevertheless, even under these conditions, from 1-2% of these triazines are formed which result in the release of small quantities of ammonia. These vapours at about 100° C. are passed through an aqueous ammonium nitrate solution at a temperature of about 60° C.-100° C. with a pH of 3-5 to an extent at which the ammonia present in the vapours is neutralized by the ammonium nitrate in solution thereby resulting in the production of ammonium nitrate as a result of the addition of nitric acid to these vapours. The ammonium nitrate from the vapours can then be used in additional processes and the steam may be condensed or released into the atmosphere.

Thus, there still remains the need for an effective method for concentrating alcohol resulting from lignocellulosic conversion processes that produce a fermentation broth that contains ammonium salts or a combination of ammonium salts or ammonia.

SUMMARY OF THE INVENTION

The present invention relates to an improved method for obtaining concentrated alcohol. More specifically, the present invention relates to the production of concentrated alcohol after distillation of a fermentation broth.

The present invention overcomes several disadvantages of the prior art by taking into account the difficulties encountered in steps carried out during the production of concentrated alcohol arising from fermentation processes. In particular, the invention is based on the inventor's observation that ammonium salts or a combination of ammonium salts and ammonia, which may be present in beer (also referred to herein as "fermentation broth") produced in lignocellulosic conversion processes that comprise ammonia or ammonium hydroxide addition, can interfere with processes employed to concentrate alcohol after standard distillation known as azeotropic breaking processes when the concentration of ammonium salts or a combination of ammonium salts and ammonia in the beer is such that the concentration of ammonium ions in the beer is at least about 1 g/kg, about 1.5 g/kg, about 2 g/kg or about 3 g/kg.

In one embodiment of the invention, the azeotropic breaking process employs a molecular sieve to remove water. The inventor has found that streams containing ammonia fed to molecular sieves used to concentrate the alcohol can result in fouling of the desiccant. Furthermore, in the case of ethanol concentration, the concentrated ethanol product may have an unacceptably high $pH_e$ value. By removing or reducing the concentration of ammonia to the vapour feed, such fouling can advantageously be reduced or prevented, which can significantly improve the performance of the molecular sieves and, in turn, the economic viability of the process. Other azeotropic breaking processes are affected by the presence of ammonia and thus are encompassed within the scope of the present invention.

In addition, by removing ammonia, the $pH_e$ of the alcohol may be lowered to within a range that meets industry standards. This is particularly advantageous for embodiments of the invention in which fuel grade ethanol is produced. Thus, according to this embodiment, when molecular sieves are utilized, not only is fouling of the resin reduced or prevented, but also the concentrated ethanol solution meets product specifications required by industry.

Accordingly, in its broadest aspect, the present invention provides a method for obtaining a concentrated alcohol solution from a lignocellulosic feedstock, said method comprising the steps of:

(i) producing a fermentable sugar solution comprising ammonium salts or a combination of ammonium salts and ammonia, wherein at least a portion of the fermentable sugar solution arises from hydrolyzing the lignocellulosic feedstock;

(ii) fermenting the sugar solution to produce a fermentation broth comprising alcohol and ammonium salts or a combination of ammonium salts and ammonia;

(iii) concentrating the alcohol in the fermentation broth by distillation to produce an alcohol-enriched vapour; and (iv) reducing the concentration of ammonia in said alcohol-enriched vapour by acid addition before or during the distillation and then further concentrating alcohol present in said alcohol-rich vapour by an azeotrope breaking process to obtain the concentrated alcohol solution.

The hydrolysis may comprise pretreatment of the lignocellulosic feedstock and then hydrolysis of the cellulose component of the feedstock with cellulase enzymes. In one embodiment of the invention, the pretreatment of the lignocellulosic feedstock is conducted with acid, including, but not limited to, sulfuric acid, to produce a pretreated lignocellulosic feedstock. According to this embodiment, the ammonium salts or a combination of ammonium salts and ammonia arise, at least in part, from the addition of ammonia or ammonium hydroxide to the pretreated lignocellulosic feedstock prior to addition of the cellulase enzymes. In another embodiment of the invention, the pretreatment of the lignocellulosic feedstock is conducted with ammonia or ammonium hydroxide to produce an alkali pretreated lignocellulosic feedstock. In this case, an acid may be added to the alkali pretreated lignocellulosic feedstock prior to enzymatic hydrolysis, which produces ammonium salts.

The hydrolysis may be carried out so as to hydrolyze both hemicellulose and cellulose present in said lignocellulosic feedstock to their respective sugar monomers. This may be conducted with either acid or alkali.

In one embodiment of the invention, the azeotropic breaking process utilizes molecular sieves. It should be understood that complete removal of ammonia may not be achieved, although it is advantageous to remove as much ammonia within practical limitations. Preferably, the amount of ammonia removed is such that the concentration of ammonia in the alcohol-enriched vapour, measured as weight of ammonia per weight of dry alcohol in the alcohol-enriched vapour, is less than about 300 ppm. For example, the concentration of ammonia in the alcohol enriched vapour may be less than about 200 ppm, about 150 ppm, about 100 ppm, about 50 ppm or about 25 ppm.

The acid may be added at the feed to the distillation, to an acid scrubber, or to a distillation column. As used herein, the term "acid scrubber" refers to a device or system for removing ammonia from a vapour stream arising from the distillation process or further concentration of the alcohol-enriched vapour. References made to acid addition "during distillation", "during the distillation" or similar phrase that may be used herein, comprise addition of acid to an acid scrubber to remove ammonia from a vapour stream arising from the distillation process. For the purposes of this invention, a distillation column may be a rectifying column. In one embodiment of the invention, the acid is added to a rectifying column, preferably via a reflux drum. Suitable acids include sulfuric acid, hydrochloric acid and phosphoric acid. A particularly preferred acid for use in the process is phosphoric acid.

The alcohol in the fermentation broth may be ethanol or butanol. In one embodiment of the invention, the alcohol is ethanol. In this case, the concentration of ethanol in the feed to the azeotropic breaking process is less than the azeotropic concentration of an ethanol-water mixture and at least about 30 percent by weight, more preferably at least about 50 percent by weight, even more preferably at least about 80 percent by weight and even more preferably at least about 94 percent by weight ethanol. The concentrated alcohol solution produced by the azeotropic breaking process preferably contains less than 1% water and at least about 97% ethanol.

BRIEF DESCRIPTION OF THE DRAWINGS

These and other features of the invention will become more apparent from the following description in which reference is made to the appended drawings wherein:

FIG. 1 is a process flow diagram for obtaining concentrated ethanol arising from a lignocellulosic conversion process according to an embodiment of the invention.

DETAILED DESCRIPTION OF THE INVENTION

The following description is of an embodiment by way of example only and without limitation to the combination of features necessary for carrying the invention into effect.

According to one embodiment of the invention, the feedstock for the process is a lignocellulosic material. By the term "lignocellulosic feedstock", it is meant any type of plant biomass such as, but not limited to, non-woody plant biomass, cultivated crops such as, but not limited to grasses, for example, but not limited to, C4 grasses, such as switch grass, cord grass, rye grass, miscanthus, reed canary grass, or a combination thereof, sugar processing residues, for example, but not limited to, baggase, beet pulp, or a combination thereof, agricultural residues, for example, but not limited to, soybean stover, corn stover, rice straw, rice hulls, barley straw, corn cobs, wheat straw, canola straw, oat straw, oat hulls, corn fiber, or a combination thereof, forestry biomass for example, but not limited to, recycled wood pulp fiber, sawdust, hardwood, for example aspen wood, softwood, or a combination thereof. Furthermore, the lignocellulosic feedstock may comprise cellulosic waste material or forestry waste materials such as, but not limited to, newsprint, cardboard and the like. Lignocellulosic feedstock may comprise one species of fiber or, alternatively, lignocellulosic feedstock may comprise a mixture of fibers that originate from different lignocellulosic feedstocks. In addition, the lignocellulosic feedstock may comprise fresh lignocellulosic feedstock, partially dried lignocellulosic feedstock, or fully dried lignocellulosic feedstock.

Lignocellulosic feedstocks comprise cellulose in an amount greater than about 20%, more preferably greater than about 30%, more preferably greater than about 40% (w/w). For example, the lignocellulosic material may comprise from about 20% to about 50% (w/w) cellulose, or any amount therebetween. The lignocellulosic feedstock also comprises lignin in an amount greater than about 10%, more typically in an amount greater than about 15% (w/w). The lignocellulosic feedstock may also comprise small amounts of sucrose, fructose and starch.

Examples of preferred lignocellulosic feedstocks include (1) agricultural wastes such as corn stover, corn cobs, wheat straw, barley straw, canola straw, oat straw, rice straw and soybean stover; and (2) grasses such as switch grass, miscanthus, cord grass and reed canary grass.

Although the use of lignocellulosic feedstocks has been described, a portion of the fermentable sugars may arise from other sources such as starch derived from cereal grains such as corn, wheat or other cereal grains or from sucrose derived from sugar cane or sugar beets.

In one embodiment of the invention, the lignocellulosic feedstock is subjected to pretreatment. The pretreatment is preferably a chemical treatment involving the addition of an acid or alkali which alters the pH of the feedstock to disrupt its fiber structure and increase its accessibility or susceptibility to being hydrolyzed in a subsequent enzymatic hydrolysis. Pretreatment methods are intended to deliver a sufficient combination of mechanical and chemical action so as to disrupt the fiber structure and increase the surface area of feedstock to make it more accessible or susceptible to cellulase enzymes. Mechanical action typically includes the use of pressure, grinding, milling, agitation, shredding, compression/expansion and chemical action may include the use of heat (often steam), acid or alkali, or solvents.

Pretreatment with acid hydrolyzes the hemicellulose, or a portion thereof, that is present in the lignocellulosic feedstock to the monomeric sugars xylose, arabinose, mannose, galactose, or a combination thereof. Preferably, the acid pretreatment is performed so that nearly complete hydrolysis of the hemicellulose and a small amount of conversion of cellulose to glucose occurs. The cellulose is hydrolyzed to glucose in a subsequent step that uses cellulase enzymes. Typically a dilute acid, at a concentration from about 0.02% (w/w) to about 2% (w/w), or any amount therebetween, (measured as the percentage weight of pure acid in the total weight of dry feedstock plus aqueous solution) is employed for the pretreatment. Preferably, the acid pretreatment is carried out at a peak temperature of about 160° C. to about 280° C. for a time of about 6 seconds to about 600 seconds, at a pH of about 0.4 to about 2.0. It should be understood that the acid pretreatment may be carried out in more than one stage, although it is preferably performed in a single stage.

One method of performing acid pretreatment of the feedstock is steam explosion, using the process conditions described in U.S. Pat. No. 4,461,648 (Foody, which is herein incorporated by reference). The pretreatment may be a continuous process as disclosed in U.S. Pat. No. 5,536,325 (Brink); WO 2006/128304 (Foody and Tolan; incorporated herein by reference); and U.S. Pat. No. 4,237,226 (Grethlein); incorporated herein by reference). Other techniques that are known in the art and that may be used as required, include, but are not limited to, those disclosed in U.S. Pat. No. 4,556,430 (Converse et al.; which is incorporated herein by reference).

Ammonia or ammonium hydroxide may be used for alkali pretreatment of the lignocellulosic feedstock. Pretreatment with ammonia or ammonium hydroxide reacts with acidic groups present on the hemicellulose to open up the surface of the substrate and may or may not hydrolyze the hemicellulose component of the feedstock. The addition of the alkali may also alter the crystal structure of the cellulose so that it is more amenable or susceptible to hydrolysis.

An example of a suitable alkali pretreatment, variously called Ammonia Freeze Explosion, Ammonia Fiber Explosion or Ammonia Fiber Expansion ("AFEX" process), involves contacting the lignocellulosic feedstock with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure. The flashed ammonia may then be recovered according to known processes. Another suitable alkali pretreatment for use in the present invention employs dilute solutions of ammonium hydroxide. Treatment of lignocellulosic feedstocks with alkali is disclosed in U.S. Pat. Nos. 5,171,592, 5,037,663, 4,600,590, 6,106,888, 4,356,196, 5,939,544, 6,176,176, 5,037,663 and 5,171,592, US2009/0053770 and US2007/0031918, which are each incorporated herein by reference.

After the pretreatment, the lignocellulosic feedstock may be treated to obtain a solids stream comprising the pretreated feedstock and an aqueous stream comprising soluble components. The aqueous stream may be separated from the solids stream by subjecting the pretreated feedstock to solids-liquid separation, using known methods such as centrifugation, microfiltration, plate and frame filtration, crossflow filtration, pressure filtration, vacuum filtration and the like. Optionally, a washing step may be incorporated into the solids-liquids separation. When an acidic pretreatment is employed, the aqueous phase comprises sugars produced by the hydrolysis of hemicellulose, as well as acid added during the pretreatment and any organic acids liberated during the pretreatment. The aqueous stream obtained from the acid pretreated feedstock may be subsequently processed to remove the mineral acid and organic acid, and then optionally fed back to the solids stream comprising the pretreated feedstock or a stream derived from the pretreated feedstock. The aqueous stream obtained from the acid pretreated feedstock may also be subjected to a fermentation to ferment the sugars. For example, xylose present in this stream may be fermented to ethanol, xylitol, butanol, or a mixture thereof.

After pretreatment, the feedstock is enzymatically hydrolyzed with cellulase enzymes to produce a stream comprising glucose. Generally, prior to enzymatic hydrolysis with cellulase enzymes, the pH of the pretreated feedstock is adjusted to within a range of about 3.0 to about 7.0, or any pH therebetween, although the pH can be higher if alkalophilic cellulases are employed. Preferably, the pH is within a range of about 4.0 to about 6.0, more preferably between about 4.5 and about 5.5. If the pretreated feedstock is alkaline (i.e., if an alkali pretreatment using ammonia or ammonium hydroxide is performed), acid is used for the pH adjustment. If the pretreated feedstock is acidic, the pH may be adjusted with ammonia or ammonium hydroxide. In either case, the neutralization results in the production of one or more ammonium salts. Ammonia may also be present in the neutralized pretreated feedstock. The presence of ammonium salts or a combination of ammonium salts and ammonia may lead to an interference with the performance of the molecular sieves used to concentrate the alcohol, as discussed below.

The process of the invention can be carried out with any type of cellulase enzymes, regardless of their source. Examples of cellulases that may be used in the practice of the invention include those obtained from fungi of the genera *Aspergillus, Humicola,* and *Trichoderma,* and from bacteria of the genera *Bacillus* and *Thermobifida.*

A suitable cellulase dosage can be about 1.0 to about 40.0 Filter Paper Units (FPU or IU) per gram of cellulose, or any amount therebetween. The FPU is a standard measurement familiar to those skilled in the art and is defined and measured according to Ghose (Pure and Appl. Chem., 1987, 59:257-268).

In commercial-scale practice, the enzymatic hydrolysis typically is carried out in a hydrolysis system which includes a number of hydrolysis reactors. The number of hydrolysis reactors in the system depends on the cost of the reactors, the volume of the aqueous slurry, and other factors. For a commercial-scale ethanol plant, the typical number of hydrolysis reactors is 4 to 12. In order to maintain the desired hydrolysis temperature, the hydrolysis reactors may be jacketed with steam, hot water, or other heat sources. Preferably, the cellulase hydrolysis is a continuous process, with continuous feeding of pretreated lignocellulosic feedstock and withdrawal of the hydrolyzate slurry. However, it should be understood that batch processes are also included within the scope of the present invention.

Although the use of pretreatment, followed by enzymatic hydrolysis using cellulase enzymes has been described to produce fermentable sugar, the feedstock may be subjected to steam and acid or alkali under conditions sufficiently harsh to hydrolyze the cellulose component of the feedstock glucose (See Grethlein, J. Appl. Chem. Biotechnol., 1978, 28:296-308, which describes strong acid hydrolysis).

Following hydrolysis of the lignocellulosic feedstock, a hydrolysate stream arising from such hydrolysis and comprising sugar is fermented to alcohol using a microorganism, such as but not limited to yeast, and the alcohol is recovered and purified by distillation. Prior to fermentation, the acid or alkali is typically neutralized. If ammonia or ammonium hydroxide is used for alkali hydrolysis or for neutralization following acid hydrolysis, this results in the formation of one or more ammonium salts. Ammonia may also be present in the neutralized hydrolysate containing glucose. The presence of ammonium salts or a combination of ammonium salts and ammonia may lead to an interference with the performance of the molecular sieves as described hereinafter.

Regardless of whether pretreatment and enzymatic hydrolysis with cellulase enzymes, or full acid or alkali hydrolysis is conducted, a sugar stream is produced that is fermented to produce a fermentation broth or "beer" containing the alcohol. For ethanol production, the fermentation is typically carried out with a *Saccharomyces* spp. yeast. Preferably, glucose and any other hexoses typically present in the hydrolysate slurry are fermented to ethanol by wild-type *Saccharomyces cerevisiae*, although genetically modified yeasts may be employed as well. For example, the fermentation may be performed with a recombinant *Saccharomyces* yeast that is engineered to ferment both hexose and pentose sugars to ethanol. Recombinant yeasts that can ferment the pentose sugar, xylose, to ethanol are described in U.S. Pat. No. 5,789,210, the contents of which are herein incorporated by reference. Furthermore, the pentose sugars, arabinose and xylose, may be converted to ethanol by the yeasts described in Boles et al. (WO 2006/096130, which is incorporated herein by reference).

Examples of other alcohol fermentation products included within the scope of the invention include, but are not limited to, butanol, 1,3-propanediol and 2,3-butanediol. Alcohols may be extracted from the fermentation broth by a solvent and then concentrated by distilling the mixture of alcohol and solvent to produce an alcohol-enriched vapour. Additional examples of microorganisms that may be employed in the fermentation include wild-type or recombinant *Escherichia, Zymomonas, Candida, Pichia, Streptomyces, Bacillus, Lactobacillus* and *Clostridium*.

Preferably, the fermentation is performed at or near the temperature and pH optima of the fermentation microorganism. A typical temperature range for the fermentation of glucose to ethanol using *Saccharomyces cerevisiae* is between about 25° C. and about 35° C., although the temperature may be higher if the yeast is naturally or genetically modified to be thermostable. The pH of a typical fermentation employing *Saccharomyces cerevisiae* is between about 3 and about 7. The dose of the fermentation microorganism will depend on several factors, such as the activity of the fermentation microorganism, the desired fermentation time, the volume of the reactor and other parameters. It should be appreciated that these parameters may be adjusted as desired by one of skill in the art to achieve optimal fermentation conditions.

The fermentation may be conducted in batch, continuous or fed-batch modes with or without agitation. Preferably, the fermentation reactors are agitated lightly with mechanical agitation. A typical commercial-scale fermentation may be conducted using a series of reactors, such as 1 to 6. The fermentation microorganisms may be recycled back to the fermentor or may be sent to distillation without recycle.

The hydrolysate slurry may also be supplemented with additional nutrients required for growth of the fermentation microorganism. For example, yeast extract, specific amino acids, phosphate, nitrogen sources, salts, trace elements and vitamins may be added to the hydrolyzate slurry to support growth of the microorganism. Ammonia compounds, such as ammonium salts, may also be added to the fermentation media and thus these salts may contribute to the ammonium salts or a combination of ammonium salts and ammonia that is present in the fermentation broth.

It should be understood that the hydrolysis and fermentation reactions can be conducted simultaneously in the same reactor, although it is preferred that the hydrolysis and fermentation are performed separately to achieve optimal temperature conditions for each reaction.

The alcohol is separated from the fermentation broth or "beer" by distillation using conventional methods. As used herein, the term "distillation" also encompasses steam and vacuum stripping.

The fermentation broth or beer that is sent to distillation is a dilute alcohol solution that contains ammonium salts or a combination of ammonium salts and ammonia. The broth may additionally contain any components added during the fermentation to support growth of the microorganisms. Microorganisms are potentially present depending upon whether or not they are removed from the beer by filtration or other means prior distillation of the beer. The beer is preferably first degassed to remove carbon dioxide and then pumped through one or more distillation columns to separate the alcohol from the other components in the beer. The column(s) in the distillation unit is preferably operated in a continuous mode, although it should be understood that batch processes are also encompassed by the present invention. Furthermore, the column(s) may be operated at any desired pressure or vacuum. Heat for the distillation process may be added at one or more points either by direct steam injection or indirectly via heat exchangers. The distillation unit may contain one or more separate beer and rectifying columns, or a distillation column may be employed that comprises an integral enriching or rectification section. As used herein, the term "distillation column" refers to a distillation column, a beer column, a distillation column with a rectification section, a rectification column or a stripper column. When separate beer and rectifying columns are employed, dilute beer is sent to the beer column where it is partially concentrated. From the beer column, the vapour goes to a rectification column for further purification.

An "alcohol-enriched vapour" is produced during the distillation process. As used herein, the term alcohol-enriched vapour is the stream fed to the azeotrope breaking process. In the case when the alcohol is ethanol, the concentration of ethanol in the ethanol-enriched vapour is equal to or less than the azeotropic concentration of an ethanol-water mixture and is at least about 30 percent by weight, more preferably at least about 50 percent by weight, even more preferably at least about 80 percent by weight and even more preferably at least about 94 percent by weight ethanol.

In accordance with the invention, the concentration of ammonia in the alcohol-enriched vapour is reduced. This may be effected by the addition of acid, prior to or during distillation, which produces ammonium salts by reaction with ammonia and/or reduces the ammonia vapour pressure in a liquid stream containing ammonium salts by reducing the pH of the stream. It should be appreciated, however, that some residual ammonia may be present in the alcohol-enriched vapour stream. Depending on the type of azeotrope breaking process, acid may be added to the azeotrope breaking process.

Acid addition may be conducted prior to any point in the process upstream of the azeotrope breaking process, or in the azeotrope breaking process or a combination thereof. For example, the acid may be added to an aqueous stream prior to distillation or to an aqueous stream or vapour stream during distillation. Examples of addition points include the feed to the distillation, or a distillation column, such as a rectifying column. When the acid is added to a rectifying column, it is preferably added via a reflux drum. Alternatively, an acid could be added to a scrubber used to remove ammonia from an alcohol-containing vapour stream in the distillation system.

Preferred acids that may be used to form the ammonium salts include hydrochloric acid, sulfuric acid and phosphoric acid. Phosphoric acid is particularly suitable since it does not corrode the process equipment as readily as other acids.

The remaining water is removed from the alcohol-enriched vapour by an "azeotropic breaking process" to produce the concentrated alcohol solution. The term "azeotropic breaking process" or "azeotrope breaking system" is meant to encompass any process for breaking the azeotrope of the alcohol-enriched vapour. This includes, but is not limited to, feeding the alcohol-enriched vapour to molecular sieves. Other azeotropic breaking processes that are encompassed by this definition include pervaporation and the addition of benzene or cyclohexane to a distillation column. After breaking the azeotrope to obtain the concentrated alcohol solution, the vapour is typically condensed to product alcohol and then denatured. If benzene or cyclohexane are used to break the azeotrope, they may be added to a distillation column to which the alcohol-enriched vapour is fed and acid may be added into such distillation column to reduce the concentration of ammonia in the alcohol-enriched vapour within said distillation column.

Preferably, the azeotropic breaking process utilizes molecular sieves. In this case, reducing the concentration of ammonia in the alcohol-enriched vapour stream reduces or prevents fouling or capacity loss of the desiccant. Any of a variety of known molecular sieves (also referred to as molecular sieve dehydrators) may be used in the practice of the invention. Molecular sieves on the market contain a zeolite material that have a crystalline lattice structure that contains openings (pores) of a precise size, usually measured in angstroms (Å). Pore sizes that are suitable will depend on the alcohol to be concentrated. Preferred zeolites for use with ethanol-enriched vapour are those of type 3 Å since the pores are 3 Å in diameter while water molecules are 2.8 Å and ethanol molecules are 4.4 Å. Furthermore, other adsorbent materials besides zeolites are available that have an affinity for water such as activated alumina. Although these adsorbents may be utilized in the practice of the invention, zeolite materials are preferred since they are typically more selective.

As would be appreciated by those of skill in the art, molecular sieves commonly use "pressure swing adsorption" to remove water from a vapourized feed stream. This refers to the fact that the molecular sieve uses a relatively high pressure when water is being removed from the feed stream and a relatively low pressure when the molecular sieve desiccant is being regenerated, i.e., having water removed from the desiccant. Typical commercial designs have two or more beds of desiccant and cycle the vapour flow through the beds to provide continuous operation. (See Development and operation of the molecular sieve: an industry standard, R. L. Bibb Swain, The Alcohol Textbook, 4$^{th}$ Edition, Nottingham University Press, 2003, pages 337-342). For example, during operation, a molecular sieve may be drying the feed vapour, while another is being regenerated (i.e., water is removed so that the desiccant is ready for the next feed cycle).

Referring now to FIG. 1, there is shown a distillation unit wherein acid is added to a reflux drum in order to reduce ammonia in the alcohol-enriched vapour. In this particular example, phosphoric acid is used to react with the ammonia to produce ammonium phosphate. Although the invention is hereinafter described with specific reference to an ethanol recovery system, it is to be understood that the principles of the invention are also applicable to the recovery of butanol, or other alcohols. Furthermore, as discussed previously, the acid may be added at other points in the distillation process besides the reflux drum.

The feed to the distillation unit 10 is beer containing ammonium salts or a combination of ammonium salts and ammonia and ethanol from fermentation of sugar produced by hydrolysis of a lignocellulosic feedstock. The beer is first fed via line 20 to a de-gas column 30 which removes carbon dioxide via line 25. The degassed beer is then sent via line 40 to a beer column 50. The beer column 50 is fed with live steam (not shown) and a bottoms product also known as "stillage" is removed from the bottom of the column. The stillage contains ammonium salts and organic material that may include unfermented sugars, residual ethanol, organic acids, lignin and fermenting microorganisms. The stillage also may contain other inorganic salts and organic material that are formed or released during processing of the lignocellulosic feedstock. Vapour containing approximately 35% ethanol is removed from the top of beer column 50 and a portion is sent to the bottom of a rectifying column 60 via lines 41 and 43, with the balance sent to the de-gas column 30 via lines 41 and 42. The rectifying column 60 comprises a series of trays 70 to maximize contact of vapour and liquid. A stream is removed from the bottom of the rectifying column 60 via line 80, which feeds a stripper 90. Stripper bottoms are removed via line 100. The top product from the rectifying column 60 that contains approximately 95% ethanol is sent to a reflux condenser 110 via line 120. Ethanol rich condensate from the reflux condenser 110 is then fed to a reflux drum 130. In this embodiment, it is at this stage of the distillation that phosphoric acid is added via line 135 to react with ammonia present in the condensate thereby forming ammonium phosphate and to reduce the pH of the condensate. The condensate is fed back to the rectifying column 60 along line 140, and the soluble ammonium phosphate in the condensate as well as soluble ammonium phosphate produced by residual acid in the condensate reacting with ammonia in the vapour at the top of the column, leaves the column in a rectifier bottoms stream through line 80 to stripper 90 and ultimately is removed with stripper bottoms in line 100. The vapour in line 120, which is substantially free of ammonia, is fed to one or more molecular sieves via line 125 to remove the residual water, thereby producing ethanol that is of a sufficient concentration to be used as fuel. The rectifier bottoms is an aqueous stream that contains residual ethanol in addition to ammonium phosphate. The majority of the residual ethanol in the rectifier bottoms is removed in stripper 90 by steam stripping and is withdrawn from the stripper with water vapour through line 95.

EXAMPLES

Example 1

The Production of Ethanol and Concentration of Ethanol from a Lignocellulosic Feedstock without acid Addition during Distillation The following example serves to illustrate that the presence of ammonium salts or a combination of ammonium salts and ammonia can compromise the performance of the molecular sieves used to concentrate ethanol that is produced as a product from a lignocellulosic conversion process. In this example, the ammonium salts or a combination of ammonium salts and ammonia are produced by neutralizing an acid pretreated feedstock with ammonium hydroxide.

The first step of the process involved size reduction of the feedstock. Wheat straw was received in bales measuring 3 feet by 3 feet by 4 feet and chopped to approximately ¼ inch in size. The straw was then mixed with water and sent to a standpipe where 93% (w/w) sulfuric acid was added to reduce the pH of the straw-water mixture to about 1.2. The slurry was pumped through piping heated by direct injection with 600 psig steam to reach a temperature of 190° C. The heated, acidified stock was held at this temperature for 1 minute as it passed through a pipe. Upon exiting the pipe, the slurry was flashed through a series of cyclones to drop the temperature to 85° C. The slurry was cooled to 50° C. and its pH then adjusted to pH 5.0 with concentrated ammonium hydroxide.

Upon acid addition, the soluble salts of potassium sulfate, sodium sulfate, and magnesium sulfate were formed, as well as the insoluble salt, calcium sulfate. Upon neutralization with ammonium hydroxide, which is soluble, the concentration of ammonium salts, including ammonium sulfate and ammonium acetate, in the slurry increased markedly.

The neutralized, cooled pretreated slurry was then pumped into a hydrolysis tank with a volume of approximately 100,000 liters. The tank was equipped with agitators to mix the slurry. The slurry consisted of 4.5% undissolved solids, and the undissolved solids consisted of 55% cellulose. Once the pretreated slurry was added to the hydrolysis tank, cellulase enzymes from *Trichoderma reesei* were added. The enzyme dosage was 35 mg protein per gram cellulose, which corresponded to a cellulase activity of 35.6 Filter Paper Units (FPU) per gram of cellulose.

The hydrolysis ran until over 90% of the cellulose was converted to glucose. The final glucose concentration in the hyrolysate was 26.0 to 28.0 g/L, with an average of 27.5 g/L. The hydrolysis slurry was pumped to a filter to separate the unhydrolyzed solid residue from the aqueous stream. The unhydrolyzed solid residue contained primarily lignin, unhydrolyzed cellulose and sand, but also insoluble salts such as calcium sulfate. The aqueous process stream was essentially free of insoluble particles and contained glucose, xylose, and arabinose sugar; the soluble salts ammonium sulfate, ammonium acetate, potassium sulfate, magnesium sulfate and a small amount of dissolved calcium sulfate, and acetic acid, soluble lignin, and other dissolved organics.

The process stream was evaporated to increase the dissolved solids concentration by using a 4-effect falling film evaporator. The glucose concentration in the evaporated stream was 60 g/L, the xylose was 30 g/L, and the acetic acid was 3.0 g/L. The evaporated stream was filtered to remove particulates.

The evaporated stream was cooled to 30° C. and pumped to a fermentor to carry out sugar fermentation with yeast.

The yeast strain was a *Saccharomyces cerevisiae* strain from Purdue University that had been genetically modified to enable it to ferment xylose, as well as glucose, to ethanol (U.S. Pat. No. 5,789,210). The fermentor, which had a volume of 90,000 liters, was fed with the evaporated sugar stream over a period of 12 hours and then run in a batch fermentation mode for 48 hours. At the end of the fermentation, the yeast cells were separated from the fermentation broth (beer).

The beer, that contained 4.9 g/kg ammonia and ammonium expressed as ammonium, was pumped to a carbon dioxide de-gas column and then to a continuous Coffey still. The first column in the still, a beer column, consisted of a number of perforated trays that permitted vapour, containing ethanol and other volatile components, to flow upwards from the bottom of the column to the top allowing for contact with the liquid flowing downwards from the top of the column to the bottom. This action allows the concentration of the volatile portions of the beer to become more concentrated as it moves from the bottom to the top of the column resulting in an ethanol concentration of approximately 40% alcohol by weight (abw). The majority of the ammonia was in the form of ammonium salts that flowed to the bottom and were discharged from the unit, although a small portion was flashed off as ammonia vapour and was carried with the ethanol to the rectifying column.

The overhead vapours from the beer column were fed to the bottom of a rectifying column where the ethanol concentration was further increased, although the concentration did not increase beyond the azeotrope point of 96% abw. From the top of the rectifying column, the vapours were pulled off with a fraction being condensed and returned to the top of the rectifying column via a reflux drum. The majority of the ammonia vapour that flashed off in the beer column exited the rectifying column with the ethanol vapour that was fed to a molecular sieve unit.

The vapours that were not condensed and refluxed back to the top of the rectifying column were first heated to 120° C. and then sent for further concentration in the molecular sieve unit. The inventor has estimated that the concentration of ammonia in the vapour fed to the molecular sieves was in the range of 500 ppm.

The molecular sieve unit consisted of two parallel units containing a three angstrom (3 Å) zeolyte. The vapour stream was sent to one of the two molecular sieves where the water vapour become trapped in the pores of the zeolyte due to its size, although the ethanol was free to pass as it is too large to enter the pores. It was determined that ammonia also was trapped in the pores. At the discharge of the molecular sieves, the purity of the ethanol was >99% with the balance of the vapour being predominantly water.

The pHe of the ethanol produced by the above-described process, after concentration by the molecular sieves, was determined to be 9.67, which was higher than the specification for its intended use as a fuel, and the concentration of ammonia and ammonium ions, as measured by ion-exchange chromatography and expressed as concentration of ammonium ions, was found to be 427 ppm.

After a period of time, all the pores of the molecular sieve were saturated with adsorbed vapours and the flow was switched to a second molecular sieve while the first one was regenerated.

Regeneration of the molecular sieves consisted of pulling a vacuum on the top of the sieve and bleeding small amounts of dried ethanol through the unit. The dry ethanol acts to strip the water vapour from the zeolyte thereby regenerating it for its next use. However, it was determined that ammonia, and compounds thereof, were not sufficiently removed from the molecular sieve unit during the regeneration step. Consequently, after a period of time, the molecular sieve could not effectively remove water, thus necessitating replacement of the zeolyte resin. Replacement was required on a monthly basis, which added significant cost to the process.

Example 2

The Production and Concentration of Ethanol from a Lignocellulosic Feedstock with Acid Addition during Distillation This example demonstrates that an acid addition step can ameliorate the problems encountered with the molecular sieves described in Example 1, namely the necessity to replace the zeolyte resin on a monthly basis and a high $pH_e$ in the ethanol product.

The production of ethanol from wheat straw was carried out as set forth in Example 1, except that phosphoric acid was added to the reflux drum of the distillation unit. The phosphoric acid fed to the reflux drum was 85% (w/w) and was introduced at a flow rate of 1.8-3.5 mL/min.

The addition of phosphoric acid to the reflux drum, which feeds the top of the rectifying column, effectively acidified the rectifying column. When the ammonia vapour comes into contact with the acidified liquid stream it forms an ammonium phosphate salt, thereby removing it from the vapour stream. The ammonia then exits the system from the bottom of the rectifying column as a salt instead of being carried through to the molecular sieves where it would foul the zeolyte resin.

In accordance with the invention, the pHe is able to be controlled so that it is in an acceptable range, i.e., between 6.5 and 9.0. In contrast to the distillation conducted without the addition of phosphoric acid to the reflux drum (Example 1), the zeolyte resin did not foul, thus eliminating the requirement for replacing it on a monthly basis.

Example 3

Determining the Concentration of Ammonium and Ammonia in a Fermentation Broth Comprising Alcohol and Ammonia in an Alcohol-enriched Vapour The concentration of ammonium ion and ammonia in a fermentation broth comprising alcohol and ammonia in an alcohol-enriched vapour is determined by first collecting a sample of the fermentation broth and vapour and analyzing the samples as described below. Ammonia is measured as its aqueous ion, ammonium ($NH_4^+$). The procedure is as follows.

Vapour is drawn from the top of the rectifying column via a sample port and through a flow meter for a defined period of time. The vapour is passed through a condenser chilled with a water jacket, or a similar equipment set-up, and the condensate and uncondensed vapour from the condenser are directed into a tightly sealed receiving flask that contains a known volume of cool acidic solution, for example 6 M hydrochloric acid. The vapour bubbles into the solution wherein water and ethanol vapours are condensed and ammonia reacts with the acid to form ammonium chloride. The final pH of the acidic solution should remain below 7 to ensure the majority (99+%) of ammonia remains in solution. Following the sampling period the volume of solution is measured to determine so the amount of water and ethanol condensed.

A portion of the ammonium-containing acidic solution is sub-sampled and diluted appropriately with water in preparation for measurement of the ammonium ion using cation exchange chromatography equipped with a conductivity detector. For example, a Dionex ICS3000 system equipped with a CS16 strong acid cation exchange column with a detection range from 0.005-0.04 g/L may be used. The measurement of ammonium ($NH_4^+$) is then converted mathematically to express the original amount of ammonia ($NH_3$) in the vapour phase.

Similarly, the combined concentration of ammonia and ammonium in the distillation feed to the beer column is measured using the Dionex cation-exchange method, described above. The feed sample is diluted appropriately with water to fall within the system detection range. The diluted sample is then filtered through a 0.2 μm syringe filter to remove any small amounts of undissolved matter prior to chromatographic analysis. The value that is obtained is the original amount of ammonium or ammonia in the liquid phase expressed as a concentration of ammonium.

I claim:

1. A method for obtaining a concentrated alcohol solution from a lignocellulosic feedstock, said method comprising the steps of:
    (i) producing a fermentable sugar solution comprising ammonium salts or a combination of ammonium salts and ammonia, wherein at least a portion of the fermentable sugar solution arises from hydrolyzing the lignocellulosic feedstock;
    (ii) fermenting the sugar solution to produce a fermentation broth comprising alcohol and at least about 1 g ammonium ions/kg fermentation broth;
    (iii) concentrating the alcohol in the fermentation broth by distillation to produce an alcohol-enriched vapour; and
    (iv) reducing the concentration of ammonia in said alcohol-enriched vapour by acid addition, before or during the distillation and then further concentrating alcohol present in said alcohol-rich vapour by an azeotrope breaking process to obtain the concentrated alcohol solution.

2. The method of claim 1, wherein in step (iv) the step of further concentrating comprises feeding the vapour to a molecular sieve.

3. The method of claim 1, wherein in step (iv) the step of further concentrating comprises pervaporation.

4. The method of claim 1, wherein acid is added at the feed to the distillation, to an acid scrubber or to a distillation column.

5. The method of claim 4, wherein the distillation column is a rectifying column.

6. The method of claim 5, wherein acid is added to the rectifying column via a reflux drum.

7. The method of claim 1, wherein the acid addition comprises addition of an acid selected from the group consisting of sulfuric acid, hydrochloric acid and phosphoric acid.

8. The method of claim 7, wherein the acid is phosphoric acid.

9. The method of claim 2, wherein the alcohol is ethanol.

10. The method of claim 3, wherein the alcohol is ethanol.

11. The method of claim 1, wherein hydrolyzing the lignocellulosic feedstock comprises pretreatment of the lignocellulosic feedstock and then hydrolysis of the cellulose component of the feedstock with cellulase enzymes.

12. The method of claim 11, wherein the pretreatment of the lignocellulosic feedstock is conducted with acid to produce an acid pretreated lignocellulosic feedstock.

13. The method of claim 12, wherein at least part of the ammonium salts or the combination of ammonium salts and ammonia in the fermentable sugar solution arises from ammonia or ammonium hydroxide added to the acid pretreated lignocellulosic feedstock to adjust the pH of the acid pretreated lignocellulosic feedstock prior to addition of the cellulase enzymes.

14. The method of claim 12, wherein the acid used for pretreatment of the lignocellulosic feedstock is sulfuric acid.

15. The process of claim 11, wherein the pretreatment of the lignocellulosic feedstock is conducted with ammonia or ammonium hydroxide to produce an alkali pretreated lignocellulosic feedstock.

16. The process of claim 15, wherein at least part of the ammonium salts or the combination of ammonium salts and ammonia in the fermentable sugar solution arises from the ammonia or ammonium hydroxide used to produce the alkali pretreated feedstock.

17. The method of claim 1, wherein hydrolyzing the lignocellulosic feedstock is carried out so as to hydrolyze both hemicellulose and cellulose present in said lignocellulosic feedstock to their respective sugar monomers.

18. The method of claim 17, wherein the hydrolysis is conducted with acid or alkali.

19. The method of claim 18, wherein the hydrolysis is conducted with acid to produce an acid hydrolysate and wherein at least part of the ammonia arises from ammonium salts produced by adding ammonia or ammonium hydroxide to the acid hydrolysate.

20. The method of claim 18, wherein the hydrolysis is conducted with ammonia or ammonium hydroxide to produce an alkali hydrolysate and wherein at least part of the ammonia arises from ammonium salts produced by adding an acid to the alkali hydrolysate.

21. The method of claim 10, wherein the concentration of ethanol in the alcohol-enriched vapour is at least about 30 percent by weight and less than the azeotropic concentration of an ethanol-water mixture.

22. The method of claim 10, wherein the concentration of ethanol in the alcohol-enriched vapour is at least about 50 percent by weight and less than the azeotropic concentration of an ethanol-water mixture.

23. The method of claim 10, wherein the concentration of ethanol in the alcohol-enriched vapour is at least about 80 percent by weight and less than the azeotropic concentration of an ethanol-water mixture.

24. The method of claim 10, wherein the concentration of ethanol in the alcohol-enriched vapour is at least about 94 percent by weight and less than the azeotropic concentration of an ethanol-water mixture.

25. The method of claim 10, wherein the concentrated alcohol solution contains at least about 97 wt % ethanol.

26. The method of claim 25, wherein the concentrated alcohol solution contain less than about 1 wt % water.

27. The method of claim 1, wherein the concentration of ammonia in the alcohol-enriched vapour is reduced by said acid addition to at most about 300 ppm.

28. The method of claim 27, wherein the concentration of ammonia in the alcohol-enriched vapour is reduced by said acid addition to at most about 200 ppm.

29. The method of claim 27, wherein the concentration of ammonia in the alcohol-enriched vapour is reduced by said acid addition to at most about 150 ppm.

30. The method of claim 27, wherein the concentration of ammonia in the alcohol-enriched vapour is reduced by said acid addition to at most about 100 ppm.

31. The method of claim 27, wherein the concentration of ammonia in the alcohol-enriched vapour is reduced by said acid addition to at most about 50 ppm.

32. The method of claim 27, wherein the concentration of ammonia in said alcohol-enriched vapour is reduced by said acid addition to at most about 25 ppm.

33. The method of claim 27, wherein the fermentation broth comprises at least about 1.5 g ammonium ions/kg fermentation broth.

34. The method of claim 27, wherein the fermentation broth comprises at least about 2 g ammonium ions/kg fermentation broth.

35. The method of claim 27, wherein the fermentation broth comprises at least about 3 g ammonium ions/kg fermentation broth.

36. The method of claim 1, wherein the concentrated alcohol solution obtained in the step of further concentrating of step (iv) has a $pH_e$, of between about 6.5 and about 9.0.

37. A method for obtaining a concentrated alcohol solution from a lignocellulosic feedstock, said method comprising the steps of:
(i) producing a fermentable sugar solution comprising ammonia or ammonium salts, wherein at least a portion of the fermentable sugar solution arises from hydrolyzing the lignocellulosic feedstock;
(ii) fermenting the sugar solution to produce a fermentation broth comprising alcohol and at least about 1.0 g/kg ammonium ions;
(iii) concentrating the alcohol in the fermentation broth by distillation to produce an alcohol-enriched vapour; and
(iv) reducing the concentration of ammonia in said alcohol-enriched vapour by acid addition, before or during the distillation, to at most about 300 ppm, and then further concentrating alcohol present in said alcohol-rich vapour by an azeotrope breaking process to obtain the concentrated alcohol solution.

* * * * *

UNITED STATES PATENT AND TRADEMARK OFFICE
CERTIFICATE OF CORRECTION

PATENT NO. : 8,273,559 B2
APPLICATION NO. : 12/548811
DATED : September 25, 2012
INVENTOR(S) : David George Geros It is certified that error appears in the above-identified patent and that said Letters Patent is hereby corrected as shown below:

ON COVER PAGE AT (56) FOREIGN PATENT DOCUMENTS:

"98/58071" should read --1998/58071--; and
"WO 2007130337" should read --2007/130337--.

COLUMN 3:

Line 54, "used produce" should read --used to produce--.

COLUMN 9:

Line 15, "*Saccharomyces* spp." should read --*Saccharomyces spp.*--.

COLUMN 10:

Line 19, "prior distillation" should read --prior to distillation--.

COLUMN 14:

Line 30, "become" should read --became--.

COLUMN 15:

Line 50, "determine so the" should read --determine the--.

COLUMN 17:

Line 38, "contain" should read --contains--.

Signed and Sealed this
Twenty-second Day of January, 2013

David J. Kappos
*Director of the United States Patent and Trademark Office*

COLUMN 18:

Line 24, "a $pH_e$, of" should read --a $pH_e$ of--.